(12) United States Patent
Hall

(10) Patent No.: US 6,841,175 B2
(45) Date of Patent: Jan. 11, 2005

(54) *CHENOPODIUM* AMBROSIOIDES EXTRACT FOR TREATING UTERINE FIBROIDS

(76) Inventor: Linneth Hall, 42 S. Waldinger St., Valley Stream, NY (US) 11580

( * ) Notice: Subject to any disclaimer, the term of this patent is extended or adjusted under 35 U.S.C. 154(b) by 0 days.

(21) Appl. No.: 10/274,596

(22) Filed: Oct. 21, 2002

(65) Prior Publication Data

US 2003/0082250 A1 May 1, 2003

Related U.S. Application Data

(60) Provisional application No. 60/343,624, filed on Oct. 22, 2001.

(51) Int. Cl.[7] .............................................. A01K 35/78
(52) U.S. Cl. ........................ 424/725; 424/774; 424/779
(58) Field of Search ............................. 424/195.1, 725, 424/774, 779

(56) References Cited

U.S. PATENT DOCUMENTS 5,595,756 A * 1/1997 Bally et al. ................. 424/450

OTHER PUBLICATIONS

Kapadia et al. Carcinogenicity of Some Folk Medicinal Herbs in Rats; J. Natl. Cancer Inst. (1978) 60 (3) pp. 683–686.*

Author: Raintree Nutrition Inc.; title: Epazote; [online] [retrieved on Dec. 30, 2002] Retrieved from the Internet: <url: http://info@rain–tree.com/epazote.htm>, dates: 1996, 2000, 2002; all pages, particularly p. 2 of 3.

Author: Animal Science Webmaster; title: Treating Livestock with Medicinal Plants: Beneficial or Toxic? *Chenopodium ambrosioides* [online] [retrieved on Jul. 30, 2001] Retrieved from the Internet: <URL: http://www.ansci.cornell.edu/plants/medicinal/epazote.html>, date: Jun. 26, 2001, all pages.

Authors: Dr. Alice B. Russell, Department of Horticultural Science; Dr. James W. Hardin, Botany, Dr. Larry Grand, Plant Pathology; and Dr. Angela Fraser, Family and Consumer Sciences; North Carolina State University. All Pictures Copyright 1997Alice B. Russell, James W. Hardin, Larry Grand, Computer programming, Miguel A. Buendia; graphics, Brad Capel; title:"Poisonous Plants of North Carolina" [online] [retrieved on Dec. 30, 2002] Retrieved from the Internet;<URL: http://www.ces.ncsu.edu/depts/hort/consumer/poison/Chenoam.htm>, date: 1997; all 2 pages.

* cited by examiner

Primary Examiner—Patricia Leith
(74) Attorney, Agent, or Firm—Nolte, Nolte & Hunter; Christopher B. Garvey

(57) ABSTRACT

A method of treating abnormal growths in a patient. The growths include: cancers, tumors, fibroids, cysts, and cystadenomas. Dry leaves and stalks of a *Chenopodium ambrosioides* plant into a dried tea. Brew the dried tea in boiled water into a tea beverage. Administer the tea beverage to the patient by having the patient drink the tea daily. The method also reduces high PSA counts.

3 Claims, 1 Drawing Sheet

CHENOPODIUM AMBROSIOIDES EXTRACT FOR TREATING UTERINE FIBROIDS

CROSS-REFERENCES TO RELATED APPLICATIONS (IF ANY)

Figure 1:
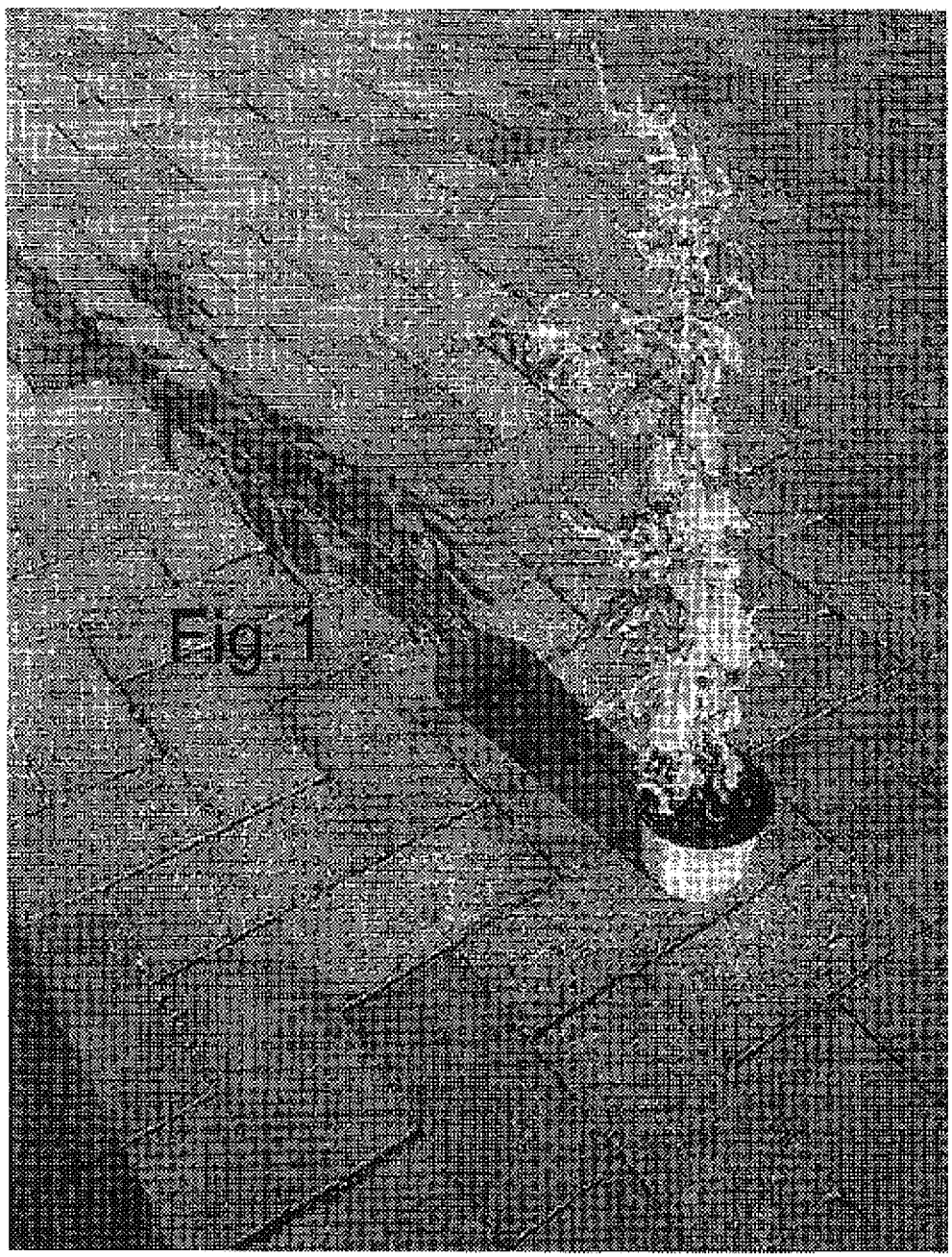

This application claims benefit of provisional Application No. 60/343,624, filed Oct. 22, 2001.

STATEMENT AS TO RIGHTS TO INVENTIONS MADE UNDER

FEDERALLY SPONSORED RESEARCH AND DEVELOPMENT (IF ANY)

None.

BACKGROUND OF THE INVENTION

1. Field of the Invention

The present invention relates to a method of treatment for growths of various types.

2. Description of Related Art Including Information Disclosed Under 37 CFR 1.97 and 1.98

A more detailed narrative on the related art is in the Information Disclosure Statement. The Art teaches that treating Livestock with Medicinal Plants of *Chenopodium ambrosioides* could be Beneficial or Toxic.

*Chenopodium ambrosioides* (Family *Chenopodiaceas*) originated in Central America, though it has been distributed to much of the world. It has been used as an anthelmintic (medicine for controlling internal parasites) for many years. In the early 1900s it was one of the major anthelmintics used to treat ascarids and hookworms in humans, cats, dogs, horses, and pigs. Usually, oil of *chenopodium* was used. It was sometimes referred to as Baltimore Oil, because of the large production facility in Baltimore that specialized in extracting the oil from the plant. *Chenopodium* was replaced with other, more effective and less toxic anthelmintics in the 1940s.

*Chenopodium* is still used to treat worm infections in humans in many countries.

Toxicity

Oil made from *Chenopodium ambrosioides* is very toxic. However, little is known about the toxicity of fresh and dried plant material, how the oil and plant are metabolized, and why toxic reactions occur. The reaction that animals have to *chenopodium* seems to vary. The art teaches that using this treatment can be risky. Signs of toxicity include: salivation, increased heart rate and respiration, changes in blood chemistry, decreased rumen motility, decreased contractions in the intestines, and convulsions. Oil of *chenopodium* can cause skin reactions, and it is dangerous to inhale.

Therefore, extreme caution should be used when treating an animal with this plant or the oil made from the plant. Other than treating the symptoms, there is no known cure to an overdose from this plant and the oil.

Uses and Efficacy

Oil of *Chenopodium* and paste from fresh plants is primarily used to treat internal parasites in humans and non-ruminant animals. However, good data on efficacy is not available. Trials done in the early 1900s usually did not have control animals to which the treated animals could be compared.

In vitro studies with oil of *chenopodium* and *chenopodium* extracts have shown that it inhibits egg development of parasites and inhibits maturation of larva. However, these results have not been confirmed in in vivo studies.

Doses with fresh plant material are harder to determine, since the quantity of compounds in the plants varies so much. The only information on fresh plant doses is for humans. One book recommends two cups of a plant/water mixture (8 leaves with water) per day for adults and 3–4 tablespoons of the mixture per day for children over five. The book warns against giving the treatment to children under 5 and pregnant women.

Some Other Uses (in humans):

| COUNTRY | ETHNOBOTANY: WORLDWIDE USES |
|---|---|
| Brazil | Stomachic, Tea, Tonic, Vermifuge |
| China | Arthritis, Analgesic, Bite (Bug), Carminative, Stomachic, Rheumatism, Vermifuge |
| Dominican Republic | Asthma, Colic, Conjunctivitis, Vermifuge |
| Elsewhere | Amebicide, Anthelmintic, Ascaricide, Asthma, Fungicide, Hookworms, Roundworms, Stimulant, Stomach, Vermifuge |
| Haiti | Ache (Stomach), Antiseptic, Parasiticide, Sore, Vermifuge |
| Mexico | Amenorrhea, Colic, Diaphoretic, Diuretic, Emmenagogueue, Fear, Nerve, Tumor, Vermifuge |
| Panama | Asthma, Dysentery, Vermifuge |
| Peru | Tumor |
| Trinidad | Amebicide, Asthma, Dysentery, Dyspnea, Fatigue, Fungicide, Palpitation, Puerperium, Sore, Stimulant, Vermifuge |
| Turkey | Asthma, Emmenagogueue, Nervine, Poison, Stimulant, Stomachic, Vermifuge |
| US | Anodyne, Dysmenorrhea, Emmenagogueue, Lactogogue, Medicine, Narcotic, Nerve, Puerperium, Vermifuge |
| Venezuela | Stomachic, Vermifuge |

SUMMARY OF THE INVENTION

*Chenopodium ambrosioides*, or Epazote, or as the plant is known under any of its above or below names, is an herb that grows to a height of 40 cm. The leaves are oval (up to 4 cm long and 1 cm wide) and toothed. The flowers are small and green, and the seeds are very small and green when fresh and black when dry. The plant has a very strong odor. Seeds can be purchased through seed catalogues.

The parts of the plant that the preferred embodiment of the present invention uses include the stalk and leaves, which are dried and then prepared as a tea.

The presently preferred embodiment does not utilize the root, seeds, nor flower. The stalk and leaves, according to the phytochemical components, are different from the root, seeds, and flower.

The presently preferred dosage is a tea, made from a quantity of about a standard commercial teabag, or about one heaping teaspoon per dosage, of dried leaves and stalk, crumbled to a tea, and brewed in boiled water to a tea. The patient drinks the tea daily.

Common Names:
  American Wormseed—U.S.
  Apazote, Epazote, Ipazote—Latin America
  Paico—Peru
  Wurmsaamen Gansefuss—Germany
  L'anserine vermifuge—France
  Erva de Santa Maria—Brazil
EPAZOTE
  Family: *Chenopodiaceae*
  Genus: *Chenopodium*
  Species: *ambrosioides*
  Common Names: Erva-de-Santa Maria, Epazote, Wormseed, Apasote, Chenopode, Feuilles A Vers, Herbe A Vers, Meksika Cayi, Paico, Pazote, Semen Contra, Semin Contra, Simon Contegras Part Used: Leaf, Plant

| DESCRIPTION | |
|---|---|
| Properties/ Actions: | Anthelmintic, Analgesic, Amebicide, Anti-microbial, Diaphoretic, Diuretic, Emmenagogueue, Lactogogue, Nervine, Parasiticide, Pectoral, Purgative, Stimulant, Stomachic, Tonic, Vermifuge, Vulnerary |
| Phytochemicals Include: | Alpha-pinene, Aritasone, Ascaridole, Ascorbic-acid, Beta-carotene, Butyric-acid, Calcium, D-camphor, EO, Ferulic-acid, Geraniol, L-pinocarvone, Leucine, Limonene, Malic-acid, Menthadiene, Methyl-salicylate, Myrcene, Niacin, P-cymene, P-cymol, Phosphorus, Safrole, Saponins, Spinasterol, Tartaric-acid, Terpinene, Terpinyl-acetate, Terpinyl-salicylate, Thiamin, Triacontyl-alcohol, Trimethylamine, Urease, Vanillic-acid |

Chemical Compounds

There are many compounds in *Chenopodium*. The compound considered to be the active ingredient is ascaridole, a monoterpene. The major components of oil of *chenopodium* are: ascaridole (60–80%), isoascaridole, p-cymene, limonene, and x-terpinene. The level of the different compounds varies depending on the part of the plant, age of the plant, and whether it is dried or fresh plant material.

The quantity of ascaridole (or other compounds) in *chenopodium* can be determined using gas chromatography and mass spectrometry (GC/MS). The major compounds in *chenopodium* can be extracted with methanol or hexanes and then sent through the GC/MS.

Some of the Compounds in *Chenopodium ambrosioides*:

Alpha-pinene—plant 440–4800 ppm

Ascaridole leaves—185–18000 ppm

D-camphor—plant

Essential oil—fruit 1830–25000 ppm, leaves 2000–3000 ppm

L-pinocarvone—plant 1040–11400 ppm

Limonene—plant

P-cymene—leaves 365–4400 ppm

P-cymol—plant 730–8000 ppm

Saponins—roots 25000 ppm

Terpinene—plant

Terpinyl-acetate—plant 75 ppm

Terpinyl-salicylate—plant 75 ppm (For a more complete list see *USDA Phytochemical and Ethnobotanical Databases*.) at: http://www.ars-grin.gov/duke/

(F) BRIEF DESCRIPTION OF THE DRAWING>(S)<

FIG. 1 is a picture of the plant used in the present invention.

(G) DESCRIPTION OF THE PREFERRED EMBODIMENT(S)

Over the past 6 years I have been working with an herbal folk treatment, an herb called semicontra (native to the Island of Jamaica) and botanical *Chenopodium ambrosioides*. Indigenously this herb has been used for treatment of many different illnesses, but my concentration is on the treatment and cure several forms of cancer as well as uterine fibroids.

For the sake of some uniformity, dosage has been achieved by drying the leaves and stems until they are the consistency of tea leaves. Quantities of the leaves are divided into dosages, each dosage being equivalent to the contents of a conventional tea bag for a commercial tea, or about 1 heaping teaspoon. The *Chenopodium ambrosioides* tea is then boiled in water like a conventional tea, and the patient then drinks the *Chenopodium ambrosioides* tea, twice daily.

Below are summaries of the outcomes in a few persons who have used the herb:

Ms P

Ms. P is a 50 year black female who was diagnosed with breast cancer in 1998. She has a history of diabetes and hypertension. Upon the diagnosis of her cancer, a CAT scan also showed "hot spots" or markers of metastasis to her portal circulation.

Ms. P was given the *chenopodium* to drink as tea, which she did for three weeks prior to initiating conventional treatment for her cancer. In the very beginning of introducing her to the herb she had it for three weeks and the hot spot her Dr saw to her portal circulation had disappeared. At the end of that time a repeated scan was done and showed that the "hot spots" had disappeared. This was before all medical treatment.

She then proceeded to start treatment by her physicians. Treatment included surgery where doctors removed her breast; followed by chemotherapy and radiation treatment. Ms P was not drinking the herbal treatment during medical treatment. She actually felt better, and post treatment tests showed no residual cancer. She returned to work.

After 20 months of wellness Ms. P begin to feel ill again. Repeated testing showed that her cancer had returned even more aggressively than before, with scans showing lung metastasis.

She was devastated, and at this time I recommended that she drink the *Chenopodium* herb tea again, using the amount equal to about that of a tea bag of the herb, twice daily. Ms P. felt more energetic, and even though her oncologist recommended repeat chemotherapy, she decided not to start the treatment just yet.

Repeated scans showed that the lung cancer was no longer there and her doctors could not explain the changes when they compared her scans before and after her herbal intake. She explains that she especially likes the improvement in her energy levels after drinking the tea. Currently Ms P's cancer is in remission. She chose not to have conventional cancer treatment on the recurrence of her cancer. She continues to drink the herb and continues with her regular check-ups. She has now returned to work.

Ms. S.

Ms. S. is a 48 year black woman with no significant medical history. She is a mother of two ages 10 and 18 years. During her monthly self-breast examination she felt two lumps to her left breast. Ms 'S' breast lumps were found in 2000. Upon testing, her mammogram and CT scan confirmed the lumps, which were described: irregular with calcification. While Ms. S. made an appointment with an oncology surgeon who planned to repeat her mammogram and CT scan to be followed by biopsy, I gave Ms. S. some of the dried herb, and I instructed her have a heaping teaspoonful as a tea twice a day.

On the fourth day of drinking the herb Ms S. noticed, on palpation, the lumps on her breast were barely felt. After seven days she did not feel them any more.

She kept her appointment for repeat mammogram and scan with her oncologist. She brought him her mammogram and scan results from the other institution of testing. The repeat mammogram and CT scan showed no lumps to the area where she had them before.

She was placed in the same position in which she received the previous CT scans upon request of the technician. There was no evidence of the lumps on the repeated CAT scans and mammogram. They were however, clearly evident on the old scan and mammogram that she had brought with her. Ms S. was sent home since there was no need for a biopsy, as explained by her doctor. In Ms S's case there was no diagnosis of cancer, only positive mammography, CAT scans and palpable lumps. To date Ms S stated that the lumps have not returned, and she continues to have regular check-ups with her doctor.

Mr. M.

Mr. M. is a 60 year-old black male, diagnosed with prostate cancer, in 2000 and treated for prostate cancer with a radical prostatectomy.

After surgery Mr. M. continued to have a Prostate Specific Antigen (PSA) of 27. He was given the herb to take twice as day as a tea. For a period of a month he continued to drink the herbal tea on a regular basis. Upon a repeated PSA testing his number was reduced to 7, and was later maintained below that number.

Mr. M. started planting his own herb and continued drinking same. To date his last medical check-up showed he is cancer free, and he is very physically active.

Ms I.

Ms I. is a 60-year-old Jamaican woman who was diagnosed with breast cancer 1998. She received all oncology treatment here in the USA. Her treatment included mastectomy, radiation and chemotherapy. Despite her aggressive treatment, Ms I's cancer returned with metastasis to her brain, as confirmed by her C T scan results, and reported by Ms I.

She had her last radiation treatment February of 2001, following which she had syncopy generalized weakness prior to returning to Jamaica. Recommendation was made to Ms I. that she should drink the herbal tea when she got to Jamaica. She had no difficulty finding the herb locally and she started drinking two cups daily since February 2001.

In October 2001, Ms I had her regular check up here in the United States with CT scans showing no evidence of brain tumors. Ms I visited the US for another checkup in July 2002 and she remains cancer free.

Liver Cancer Patient

Ms I reported that, since she had made had such remarkable progress in her health, she told her local doctor in Jamaica about the herb that she had been drinking for her cancer. Her doctor who, was impressed, started to prescribe the herb as treatment to some of his cancer patients.

Mr. D

Mr. D. is a 70-year-old patient of Ms I's doctor with a history of prostate cancer. He was reported to have advanced-stage liver cancer, and was given a life expectancy of six months. He chose not to have chemo or radiation therapy upon diagnosis of his cancer. His doctor informed him of the herb, and in February 2001 he started drinking two cups of the tea per day. He felt well for 9 months while he continued to drink the herbal tea. He has no weight loss, jaundice or abnormal lab work, was walking 2 miles daily, swimming and working. After 9 months, Mr. D. began to lose his appetite and had problems with constipation. He consulted with a Japanese holistic doctor who gave him some enzymatic capsules and mushroom tablets to take. Mr. D also modified his diet and began drinking the juice of several fruits and vegetables daily. He removed red meat from his diet, eating only chicken and fish. He continues to drink the herbal tea in addition to the changes in his diet. He noticed that his health and appetite improved progressively over time. He had regular checkups with his doctor who noticed that the CT scans showed his liver cancer diminishing in size. In April 2002, repeated scans showed no evidence of Mr. D's liver cancer.

Mr. D's doctor and his colleagues in the medical field all call the recovery miraculous. To date, Mr. D has returned to work, enjoys a healthy, active lifestyle and continues to drink the herb.

Ms M

Ms M. is a 47-year-old woman with 22-year-old daughter. She has history of severe menstrual pain, which got more severe the last four months. About 2001, her gynecologist, on examination, told her she has a uterine fibroid (myoma, or leiomyoma) the size of a grapefruit, and she needed to have surgery to remove the tumor. During her doctor's examination he asked her to feel the tumor, which she stated she did feel.

Ms M. was introduced to the herb as a treatment for most female GYN problems and drank the herbal tea for three weeks, using one cup of tea brewed from a teaspoon of the dried herb. During this time she made an appointment with another doctor to have a Sonogram to have a second opinion on the fibroid. She did have the sonogram and the results showed:

she had no fibroids in her uterus, and in fact the "uterine muscle was smooth."

Three months after the Sonogram, during this three months, Ms M had been drinking the herb a week prior to having her menstrual cycle. She has stated that she no longer has pain during this time, and her bleeding has no clots as before, and the flow is normal. To date, Ms. M continues to have regular checkups that show no evidence of fibroids.

Ms "H"

Ms "H" who was a 37 year old female with no children, was diagnosed with fibroids in 2001 the size of three months pregnancy. Ms "H" was introduced to the herb shortly thereafter as a treatment for her fibroids following a MRI confirmation. She had one cup daily brewed from a teaspoon of the dried herb for a period of one month.

For the first two weeks she felt no changes to the size of her fibroids, which she self-monitored by palpation and located two finger-breadths above her umbilicus in a lying position. She was encouraged to continue the herb anyway which she did for another week.

After a full month the fibroids were felt two finger-breath below the umbilicus with evidence of shrinking in size. Two weeks later she stated she stopped drinking the herb because she think her fibroids was getting bigger and in fact was felt above the initial marker from her umbilicus.

One month following, Ms "H" confessed that she was diagnosed as pregnant and was now two months in the pregnancy. She also stated her Gynecologist stated, "its a shock" to her that she got pregnant with the size fibroids she has. The doctor also stated that the fibroids grew more since she became pregnant due to the increased estrogen levels during the first trimester of pregnancy. Ms "H" was convinced she got pregnant when the fibroids shrank during the month she had the herb. She introduced the herb to her friend who has had two failed in-vitro pregnancies.

Due to fibroids, Ms "H" was unable to get pregnant before now and this is her first. She has discontinued drinking the herb due to her pregnancy and the unknown side effects. Her pregnancy was considered "high risk" at ten weeks. Her Doctor was hoping the fibroids would shrink during the hormonal changes in the second trimester so she can have a continued successful pregnancy. Ms H continued at high risk during her pregnancy up to 37 weeks, and delivered a healthy baby.

To date, the baby is 5 months old. Ms H is breastfeeding and therefore has discontinued drinking the herbal tea. She hopes to resume as soon as she stops breastfeeding her baby, since she still has problems with fibroids.

Ms K

Ms K is a 34-year-old black female who was diagnosed with intrauterine fibroids at age 24. Since then she has had one myomectomy (fibroid removal) at age 26 and another at age 32. Ms K had recurrence of her fibroids a year after her second surgery. This time the fibroids were pressing against her kidneys and colon causing severe pain, constipation and vomiting. Ms K sought medical treatment and based on her sonogram and CAT scan the fibroids were also outside of her uterus. Her doctors recommended that she have a hysterectomy in January 2002. Ms K refused to have surgery because she wanted to have children. Her doctor prescribed laxatives and pain medication. Ms K decided to start drinking *Chenopodium* tea. She had one cup of tea daily for 3 weeks, during which time her bowel movements became regular and the pain was alleviated. She continued to drink the herbal tea for another month during which time she felt much better. Ms K was encouraged to see her doctors again and have repeated evaluations of her fibroids, but she is non-compliant. To date, she is feeling better but because she has not visited her doctors, there is no current clinical evaluation of her fibroids.

Mrs. G

Mrs. G is a Caucasian woman of Welsh-Irish-English-Italian ancestry, born 1921, who has been was suffering since 1964 from pseudomixoma peritonia; which is a mucaginous cyst or non-invasive cancer, also called a benign psuedomucinous cystadenoma.

The cyst was first removed in fall 1964, in a hysterectomy, which removed a benign psuedomucinous cystadenoma at St. John hospital Yonkers.

Since then Doctors have monitored its accelerating growth. After the initial operation, the cyst took about 16 years to grow back to uncomfortable size.

A second operation about Oct. 9, 1980 removed a benign pseudomixoma peritonei [benign psuedomucinous cystadenoma]

13 years later, in July 1993, Dr. Clark in Fla. removed 3 liters of gelatinous material—psuedomyxoma peritonei About eight years later, Apr. 27, 1999, Dr. Clark in Fla. removed less than 3 liters of gelatinous material—psuedomyxoma peritonei, and 6 inches of intestines.

About two years later, Aug. 29, 2001 a CAT scan showed golf ball or lemon size growth, about 6 cm.×5 cm. For simplicity in calculation, I'm assuming the shape is approximately a cylinder, which would be a volume of about:

Pi*radius [squared]*length=3.14*[[5/2 cm.] squared]*6 cm.=about 118 cc

Prior to starting the tea, Mrs. G had been noticing a puss-like discharge in her stool, which she associated with her cyst.

In Early November 2001, Mrs. G began drinking the tea daily

She mentioned about May 5, 2002 that she had not seen the puss-like discharge in her stool, since she started taking the tea.

About Mar. 15, 2002 the latest CAT scan showed that the mass had changed shape to 4.5×7 cm.

Again assuming a cylinder, 3.14*[[4.5/2 cm.] squared]*7 cm.=about 111 cc

So, after several months of drinking the tea, there was no growth, but instead, there was a very slight reduction in total volume, about 6%.

Mrs. G's next CAT scan is scheduled to be Nov. 5, 2002.

What is claimed is:

1. A method of treating uterine fibriods to a person in need thereof; said method comprising:

administering a dosage of tea beverage to a patient, wherein said tea beverage is prepared by drying leaves and stalks of a *chemopodium ambrosiodes* plant to form a dried tea;

brewing said dried tea in boiled water to produce a tea beverage;

wherein said administration comprises drinking the tea beverage daily.

2. A method according to claim 1 wherein said dosage is a heaping teaspoon of the dried tea in about one cup of boiled water; to make one cup of tea beverage, wherein said administration comprises drinking the tea beverage in a frequency between once and twice daily.

3. A method according to claim 2 in which the dosage for an individual patient is started at one dose per day;

the uterine fibroid is monitored; and if the growth of the uterine fibroid is not stopped or reduced, the dosage is increased to twice daily.

* * * * *

UNITED STATES PATENT AND TRADEMARK OFFICE
CERTIFICATE OF CORRECTION

PATENT NO. : 6,841,175 B2
DATED : January 11, 2005
INVENTOR(S) : Hall

It is certified that error appears in the above-identified patent and that said Letters Patent is hereby corrected as shown below:

<u>Column 8,</u>
Line 23, please change "chemopodium" to correctly read: -- chenopodium --.

Signed and Sealed this

Fifth Day of April, 2005

JON W. DUDAS
*Director of the United States Patent and Trademark Office*